US010245014B2

(12) United States Patent
Yang

(10) Patent No.: US 10,245,014 B2
(45) Date of Patent: Apr. 2, 2019

(54) DEVICE OF AUTOMATIC MECHANICAL WOUND OPENER FOR HEAD AND NECK SURGERY

(71) Applicant: NATIONAL TAIWAN UNIVERSITY HOSPITAL

(72) Inventor: Tsung-Lin Yang, Taipei (TW)

(73) Assignee: NATIONAL TAIWAN UNIVERSITY HOSPITAL, Taipei (TW)

( * ) Notice: Subject to any disclaimer, the term of this patent is extended or adjusted under 35 U.S.C. 154(b) by 0 days.

(21) Appl. No.: 15/217,239

(22) Filed: Jul. 22, 2016

(65) Prior Publication Data

US 2016/0324516 A1    Nov. 10, 2016

Related U.S. Application Data

(63) Continuation-in-part of application No. 14/047,104, filed on Oct. 7, 2013, now Pat. No. 9,526,485.

(51) Int. Cl.
*A61B 17/02* (2006.01)
*A61B 90/50* (2016.01)
*A61B 90/57* (2016.01)

(52) U.S. Cl.
CPC .......... *A61B 17/0206* (2013.01); *A61B 90/50* (2016.02); *A61B 2090/571* (2016.02)

(58) Field of Classification Search
CPC . A61B 17/02; A61B 17/0206; A61B 17/0218; A61B 90/50
See application file for complete search history.

(56) References Cited

U.S. PATENT DOCUMENTS

| 4,989,587 A | 2/1991 | Farley |
| 5,795,291 A * | 8/1998 | Koros ..................... A61B 17/02 600/213 |
| 5,902,233 A * | 5/1999 | Farley ................. A61B 17/0206 600/213 |
| 7,654,954 B1 | 2/2010 | Phillips et al. |
| 2009/0287062 A1* | 11/2009 | Farley ................. A61B 17/0206 600/231 |

\* cited by examiner

*Primary Examiner* — Si Ming Ku
(74) *Attorney, Agent, or Firm* — Muncy, Geissler, Olds & Lowe, P.C.

(57) ABSTRACT

Provided is a device of automatic mechanical wound opener for head and neck surgery. The device includes a wound opener including: a fixed unit and a plurality of drawing units, and at least one of the drawing units being movably connected on the fixed unit, wherein each of the drawing units includes a first arm, a second arm, and a blade connected to the second arm; wherein the first arm is connected to the fixed unit by one end thereof and to the second arm by the other end thereof; the second arm can be adjusted to an needed included angle relative to the first arm; and at least one of the blades includes an extension plate connected to an end of a plate part of the blade, and the extension plate is connected to the second arm for shortening the spacing between two blades.

11 Claims, 9 Drawing Sheets

DEVICE OF AUTOMATIC MECHANICAL WOUND OPENER FOR HEAD AND NECK SURGERY

CROSS-REFERENCES TO RELATED APPLICATIONS

This application is a continuation-in-part of U.S. application Ser. No. 14/047,104, filed on Oct. 7, 2013, which is incorporated herewith by reference.

BACKGROUND OF THE INVENTION

1. Field of the Invention

The present invention relates to a wound opener for head and neck surgery; more particularly, relates to a device of automatic mechanic wound opener applied to support a wound for head and neck surgery and thus conveniently introduce endoscopes or robotic arms into the wound to evaluate and further treat lesions of head and neck, so that the surgery can be performed smoothly, the wound size can be reduced, and the wound can be effectively concealed from visible.

2. The Prior Arts

Head/neck surgery is usually performed by an open operation. An incision made at head/neck and soft tissues are pulled outwardly for treating lesions. Hence, the traditional head/neck surgery may result in an obvious visible wound. Furthermore, the issues pertinent to postoperative care and cosmetic results of the wound are also encountered.

Endoscopes or robotic arms can be used for solving these problems. During the surgery, an operative space is required to be created at first for smoothly introducing the endoscopes or robotic arms to evaluate and further treat lesions. The head and neck of a human body has many different perplexing soft tissues, like muscles, nerves, glands and vessels. In addition, head and neck have smaller spaces than the other parts of the body for dissection. Until now, no proper wound opener is available for head and neck surgery when the endoscopes or robotic arms are used. As a result, the endoscopes or robotic arms cannot be operated easily, which makes surgical procedures difficult.

Hence, it is required to provide a novel device of automatic mechanical wound opener for head and neck surgery to improve the above-mentioned shortcomings.

SUMMARY OF THE INVENTION

The main objective of the present invention is to provide a mechanic wound opener to support a wound for introducing endoscopes or robotic arms to evaluate and further treat lesions of head and neck, so that the operative space can be increased and thus the surgery can be performed smoothly. Meanwhile, the wound size can be reduced and the wound can be effectively concealed from visible.

To achieve the above objective, the present invention provides a device of automatic mechanical wound opener for head and neck surgery. The device comprises a wound opener, and the wound opener comprises a fixed unit and a plurality of drawing units connected thereto. At least one of the drawing units is movably connected on the fixed unit, and each of the drawing units includes a first arm, a second arm connected with the first arm, and a blade connected to the second arm, where the first arm is connected to the fixed unit at one end thereof and to the second arm at the other end thereof. The second arm can be disposed at a needed included angle relative to the first arm; and at least one of the blades comprises an extension plate that is connected to the second arm for shortening the spacing between the two blades but keeping a larger space between two drawing units at the first and second arms thereof.

In an embodiment of the present invention, the device further comprises an operating frame connected to one end of the wound opener by a locking unit. The operating frame comprises a supporting unit and a connecting unit movably mounted on the supporting unit. The supporting unit comprises a first adjusting base and a support rod movably mounted thereon. Further, the connecting unit comprises a second adjusting base movably mounted on the support rod and an extension rod movably mounted on the second adjusting base.

In one aspect of the embodiment, the extension rod is, but not limited to, perpendicular to the support rod.

In another embodiment of the present invention, the drawing unit can be moved along the fixed unit to and positioned at a desired position by an adjusting unit. In one aspect of the embodiment, the fixed unit has a plurality of dental grooves. The adjusting unit comprises a clamp, a controlling member, and a moving member. The clamp is mounted on the moving member, and the moving member is sleeved on the fixed unit and has a chamber for inserting the controlling member therein. The controlling member comprises an operating handle and a plurality of teeth corresponding to the plurality of dental grooves formed on the fixed unit.

In a further embodiment of the present invention, the blade is pivotally connected to the second arm so that the blade can be pivotally adjusted to a desired included angle relative to the first arm according to the actual operation requirements.

In one aspect of the embodiment, The blade can include a plate part, an extension plate connected to one end of the plate part, and a knob disposed on the extension plate. The second arm can include a hole for inserting the knob therein such that the blade can be pivoted relative to the second arm to adjust the slope of the plate part.

In another aspect of the embodiment, the blade can be shaped in the form of, but not limited to, long plate. The length, width, or even shape of the blade can be designed according to the actual operating needs.

In yet another aspect of the embodiment, for decreasing the size of incision, each of the blades can be pivoted relative to the respective second arm around the knob disposed in the extension plate, such that the plate parts of two blades have a relative smaller spacing. The extension plate has a suitable length depending on the needed spacing between two blades. In one aspect of the embodiment, the plate part of the blade can be, but not limited to, perpendicular to the extension plate.

In a further embodiment of the present invention, the first arm and the second arm can be connected to each other in a pivotal manner. As such, the second arm can be adjusted to a needed included angle relative to the first arm to meet the operation requirements.

Accordingly, a novel device of automatic mechanical wound opener for head and neck surgery can be obtained.

BRIEF DESCRIPTION OF THE DRAWINGS

The present invention will be better understood from the following detailed description of the preferred embodiment according to the present invention, taken in conjunction with the accompanying drawings, in which.

DETAILED DESCRIPTION OF THE PREFERRED EMBODIMENT

The following description of the preferred embodiment is provided to understand the features and the structures of the present invention.

Figure 1:
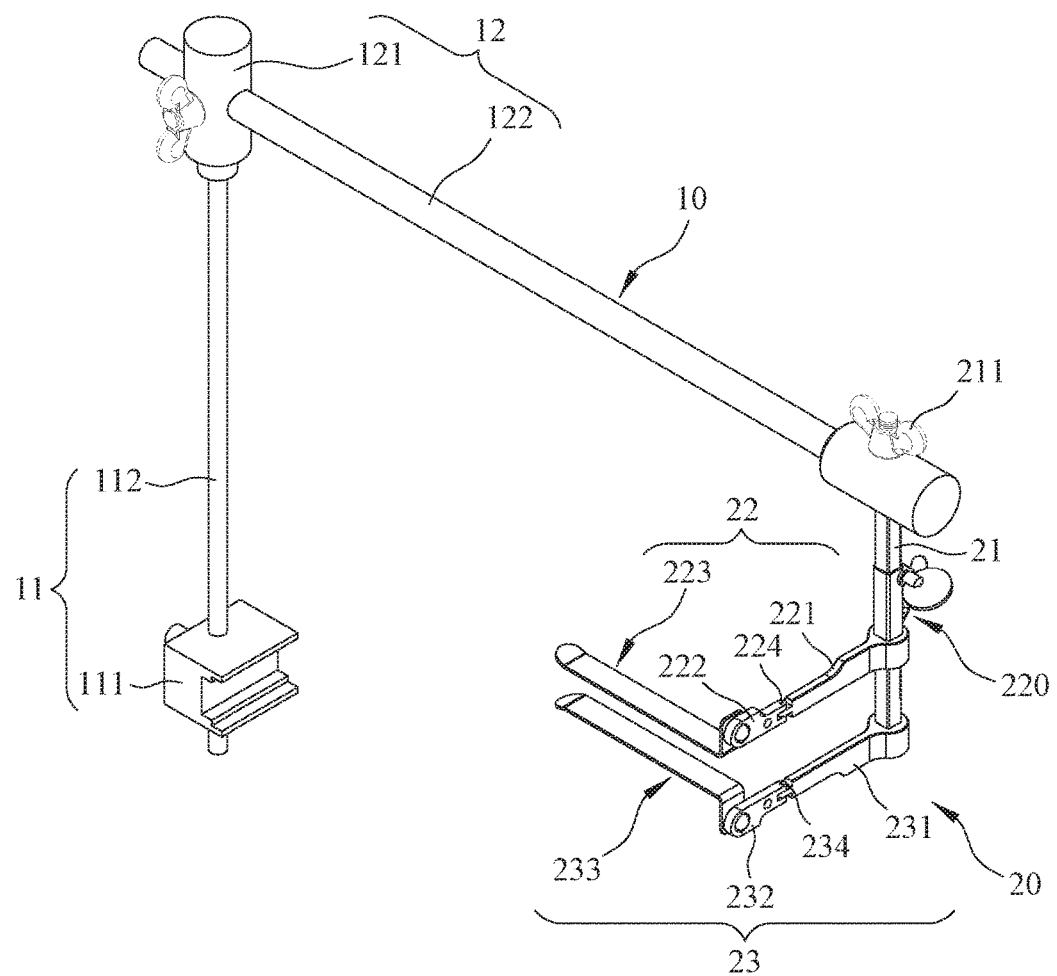
FIG. 1 is a perspective view of a device of automatic mechanical wound opener according to an embodiment of the present invention.

Referring to FIG. 1, which shows a perspective view of a device of automatic mechanical wound opener according to one embodiment of the present invention. As shown in FIG. 1, the device of automatic mechanical wound opener comprises an operating frame 10 and a wound opener 20, and the wound opener 20 can be fixed at an end of the operating frame 10 by a locking unit 211.

The operating frame 10 comprises a supporting unit 11 and a connecting unit 12 movably connected therewith. The supporting unit 11 comprises a first adjusting base 111 and a support rod 112 movably mounted thereon. Further, the connecting unit 12 comprises a second adjusting base 121 movably mounted on the support rod 112 and an extension rod 122 movably mounted on the second adjusting base 121. Generally, the extension rod 122 may be, but not limited to, perpendicular to the support rod 112. The support rod 112 can be movably adjusted to a desired height, and the extension rod 122 can be adjusted to a desired direction and length.

The wound opener 20 is mounted at an end of the extension rod 122 of the connecting unit 12 of the operating frame 10. The wound opener 20 comprises a fixed unit 21 and two drawing units (i.e., a first drawing unit 22 and a second drawing unit 23) connected to the fixed unit 21. In this embodiment, the first drawing unit 22 is movably connected on the fixed unit 21, but the second drawing unit 23 is fixedly connected to the fixed unit 21. As such, only the first drawing unit 22 can be adjusted along the fixed unit 21 to a desired position. In another aspect of the embodiment, the second drawing unit 23 can also be designed to be movably connected on the fixed unit 21 in the same way of the first drawing unit 22.

Figure 2:
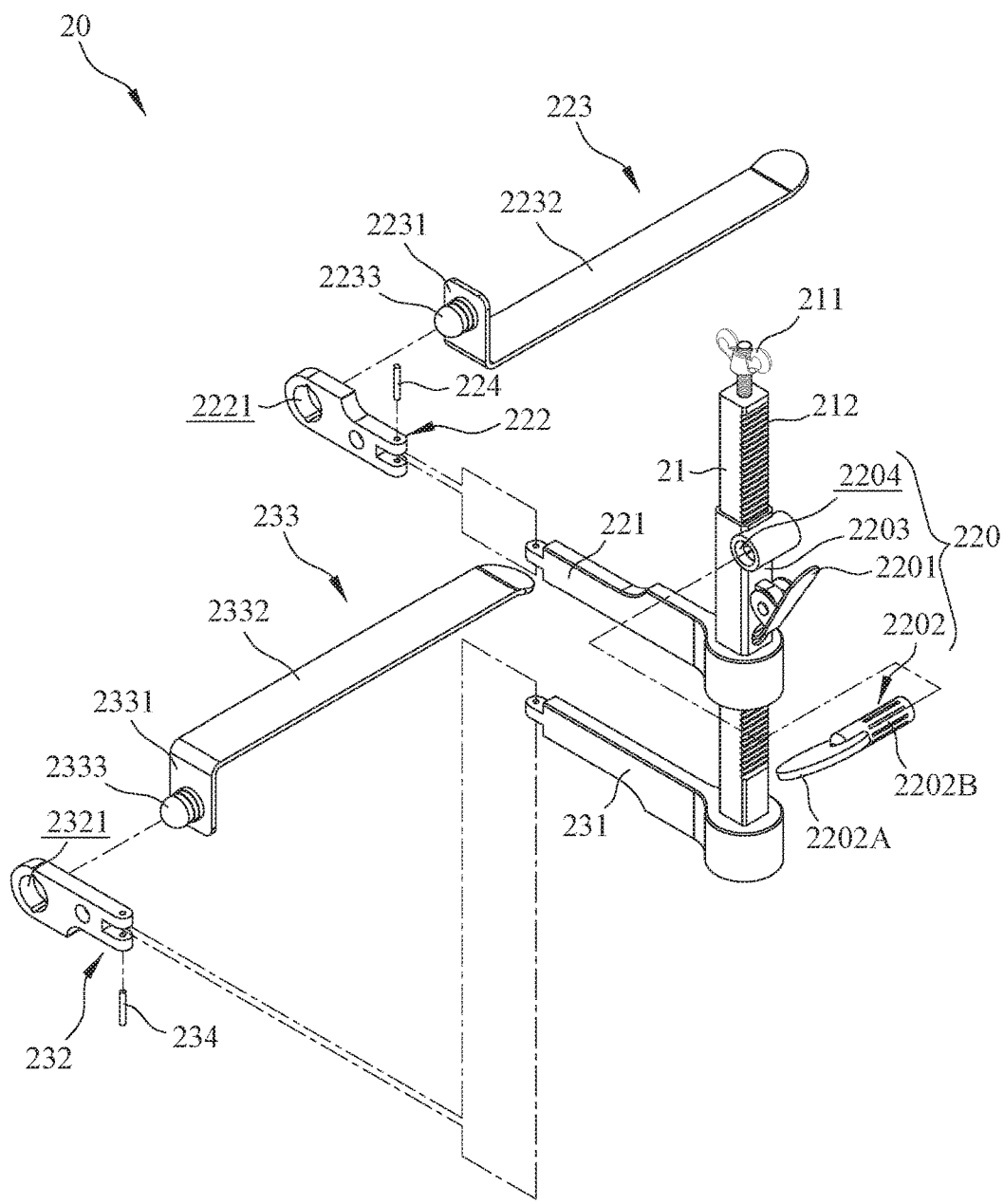
FIG. 2 is an exploded view of a wound opener according to an embodiment of the present invention.
Figure 3:
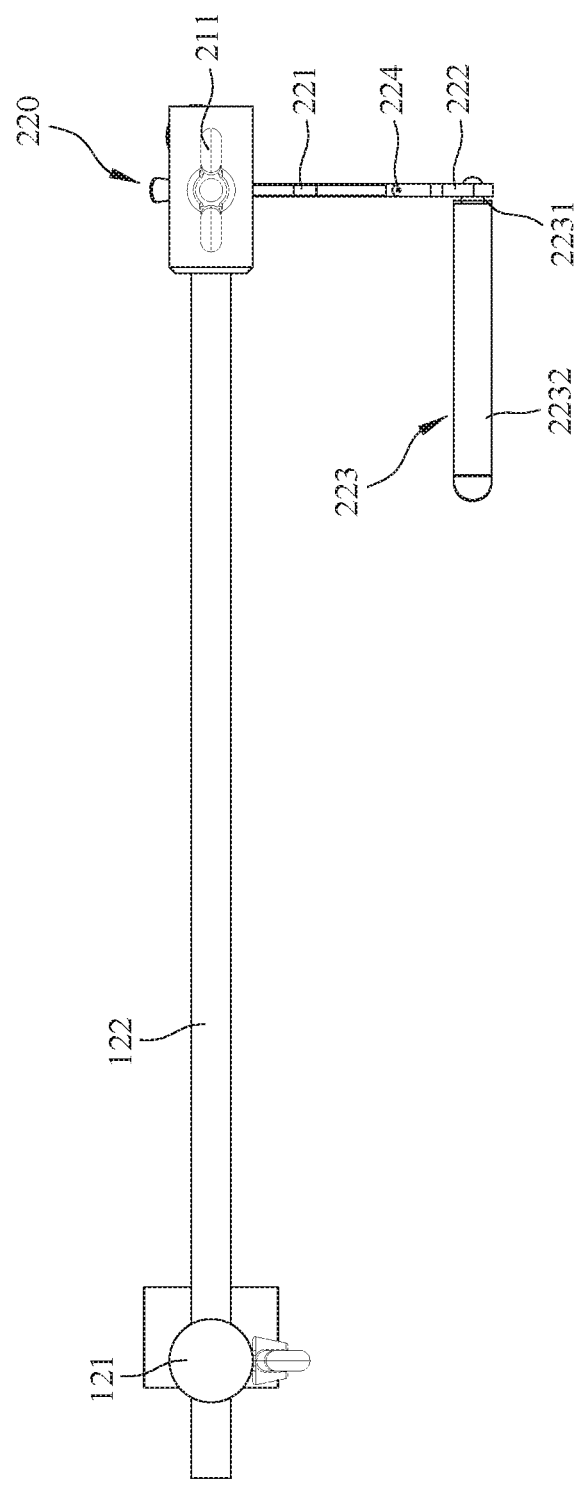
FIG. 3 is a top view of the device of automatic mechanical wound opener of FIG. 1 according to an embodiment of the present invention.
Figure 7:
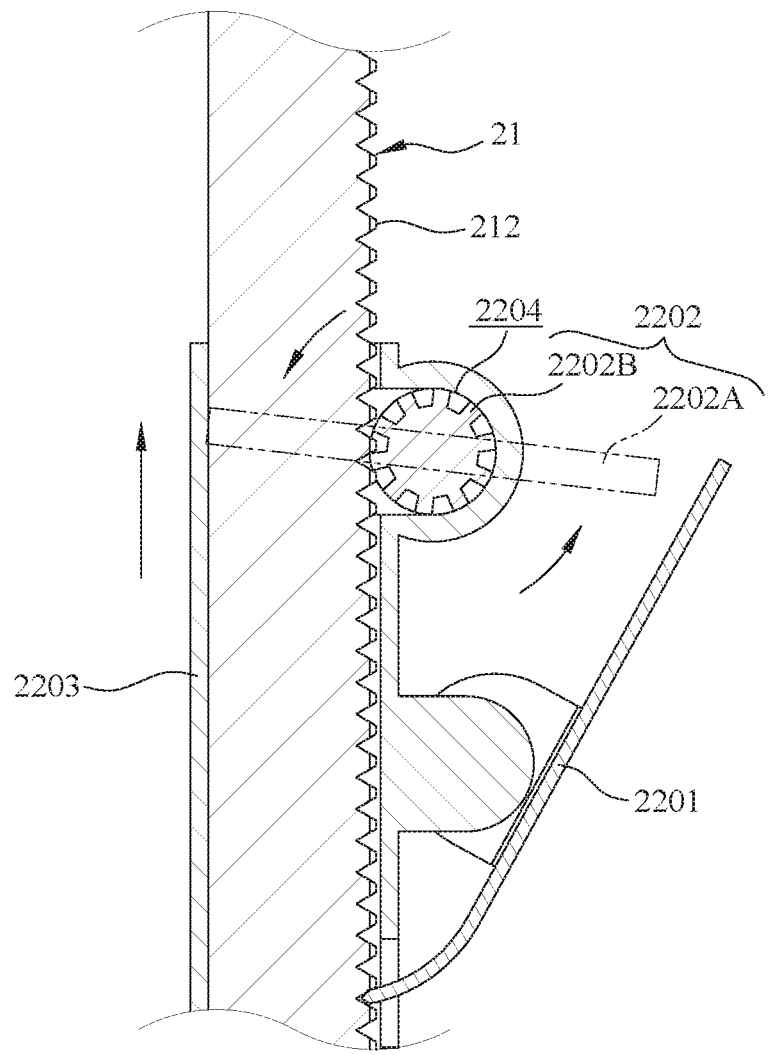
FIG. 7 is a sectional view of the adjusting unit according to an embodiment of the present invention.

FIG. 2 is an exploded view of a wound opener according to one embodiment of the present invention, and FIG. 3 is a top view of the device of automatic mechanical wound opener according to one embodiment of the present invention. Referring to FIGS. 1, 2 and 3, the first drawing unit 22 is movably connected to the fixed unit 21 by an adjusting unit 220. The adjusting unit 220 may comprise a clamp 2201, a controlling member 2202 and a moving member 2203. Also referring to FIG. 7, the clamp 2201 is mounted on the moving member 2203, and the moving member 2203 is sleeved on the fixed unit 21 and has a chamber 2204 for inserting the controlling member 2202 therein. The controlling member 2202 comprises an operating handle 2202A and a plurality of teeth 2202B corresponding to a plurality of dental grooves 212 formed on the fixed unit 21. The dental grooves 212 are engaged with the teeth 2202B of the controlling member 2202 when the controlling member 2202 is inserted into the chamber 2204. The controlling member 2202 can be inserted into the chamber 2204 from either one of both sides thereof depending on the operating space for not interfering with the operation of endoscopes or robotic arms. For example, as shown in FIG. 2, the controlling member 2202 is inserted from the left side of the chamber 2204, but it may be inserted from the right side thereof. In addition, the clamp 2201 can be engaged with the dental grooves 212 for positioning the moving member 2203 when the moving member 2203 is moved to a desired position.

For moving the adjusting unit 220 upward, the operating handle 2202A of the controlling member 2202 is rotated counterclockwise so that the teeth 2202B are engaged with the dental grooves 212 to make the moving member 2203 move upwardly along the fixed unit 21. Meanwhile the tip of the clamp 2201 is detached from a dental groove 212 first and then attached into the next dental groove 212 along with the movement of the moving member 2203. It is noted that the controlling member 2202 cannot be rotated clockwise to move the adjusting unit 220 downward owing to being stuck of the tip of the clamp 2201 in the dental groove 212. As such, the wound could be opened gradually and fixed. When the adjusting unit 220 or the first drawing unit 22 is adjusted or moved to a suitable position, the rotational action of the controlling member 2202 is stopped, and the tip of the clamp 2201 grips in the dental groove 212 such that the adjusting unit 220 is fixed at the final desired position. On the contrary, for moving the adjusting unit 220 downward, the tip of clamp 2201 is detached continually from a dental groove 212 first by pressing and holding an end of the clamp 2201. Then, the operating handle 2202A of the controlling member 2202 is rotated clockwise until a desired position is reached and finally the clamp 2201 is released.

The first drawing unit 22 may include a first arm 221 connected with a second arm 222, and a first blade 223 connected to the second arm 222. The first arm 221 is mounted to the fixed unit 21 by the adjusting unit 220 at one end thereof and connected to the second arm 222 by the other end thereof. Moreover, the first arm 221 and the second arm 222 are pivotally connected by a pivot pin 224. As such, the second arm 222 can be disposed at a needed included angle relative to the first arm 221 according to the actual operation requirements. The included angle may be 180° or less. In a similar way to the first drawing unit 22, the second drawing unit 23 can include a first arm 231, a second arm 232, and a second blade 233. Also, the first arm 231 and the second arm 232 of the second drawing unit 23 are pivotally connected by a pivot pin 234.

As shown in the figures, the first blade 223 may include a plate part 2232, an extension plate 2231 connected to one end of the plate part 2232, and a knob 2233 disposed on the extension plate 2231. The second arm 222 may include a hole 2221 for inserting the knob 2233 therein such that the first blade 223 can be pivoted relative to the second arm 222 to adjust the slope of the plate part 2232. In a similar way to the first blade 223, the second blade 233 may also include a plate part 2332, an extension plate 2331 connected to one end of the plate part 2332, and a knob 2333 disposed on the extension plate 2331. The second arm 232 includes a hole 2321 for inserting the knob 2333 therein such that the second blade 233 can be pivoted relative to the second arm 232 to adjust the slope of the plate part 2332. Therefore, the plate part 2232 of the first blade 223 and the plate part 2332 of the second blade 233 can be disposed horizontally, aslant or vertically relative to a horizontal plane. In addition, the shape or the length of the plate parts 2232 and 2332 is not particularly limited. It can be shaped in the form of long plate as the embodiment. Furthermore, the first blade 223 and the second blade 233 can be disposed on either side of the second arm 222 or 232 depending on the wound location of the patient; namely, the knob 2233 of the first blade 223 or the knob 2333 of the second blade 233 can be inserted into the hole 2221 or 2321 from either one of both sides thereof. For example, as shown in FIG. 2, the knob 2233/2333 is inserted from the right side of the hole 2221/2321, but it may be inserted from the left side thereof.

In this embodiment, the first blade 223 is connected with the second arm 222 by an extension plate 2231, and the second blade 233 is also connected with the second arm 232 by an extension plate 2331. However, the extension plate can be disposed only on the first blade 223 or on the second blade 233, or be disposed on each of them. The length of the extension plate 2231 or 2331 is not particularly limited, but can be chosen depending on the needed spacing between the two blades for the incision. Moreover, the plate part of the blade may be, but not limited to, substantially perpendicular to the extension plate.

Figure 4:
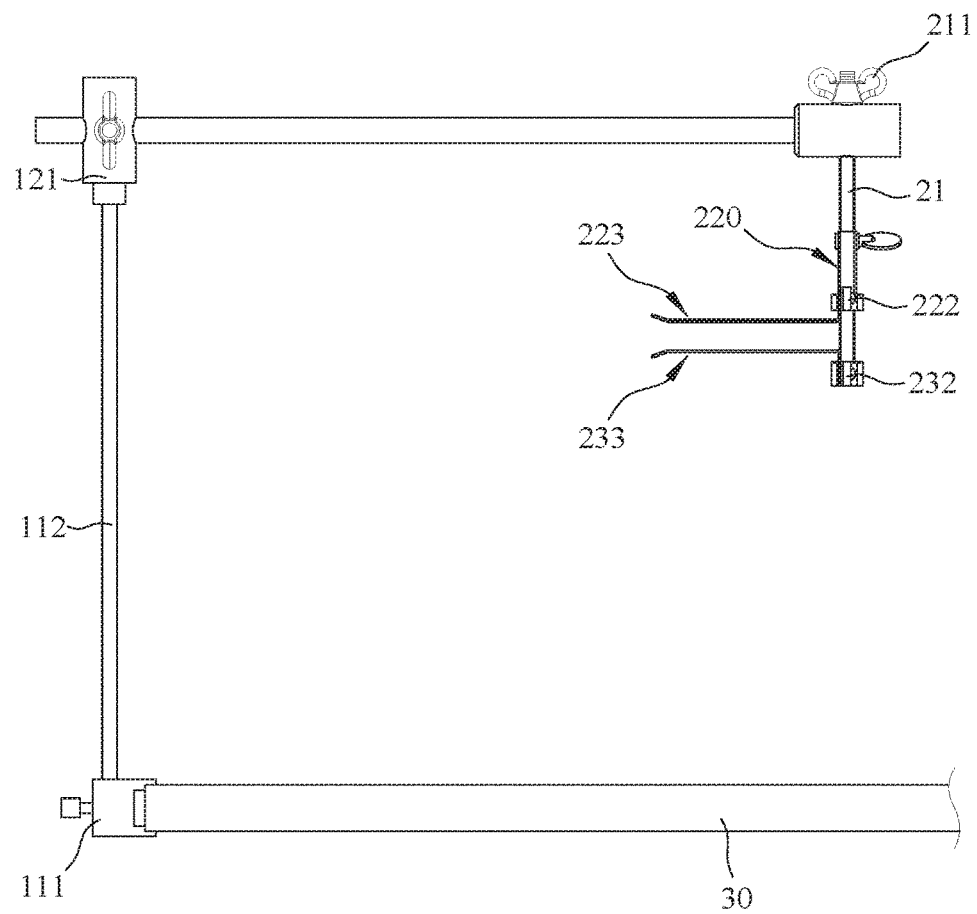
FIG. 4 is a side view of the automatic mechanical wound opener according to an embodiment of the present invention, which is mounted on an operating bed.
Figure 5:
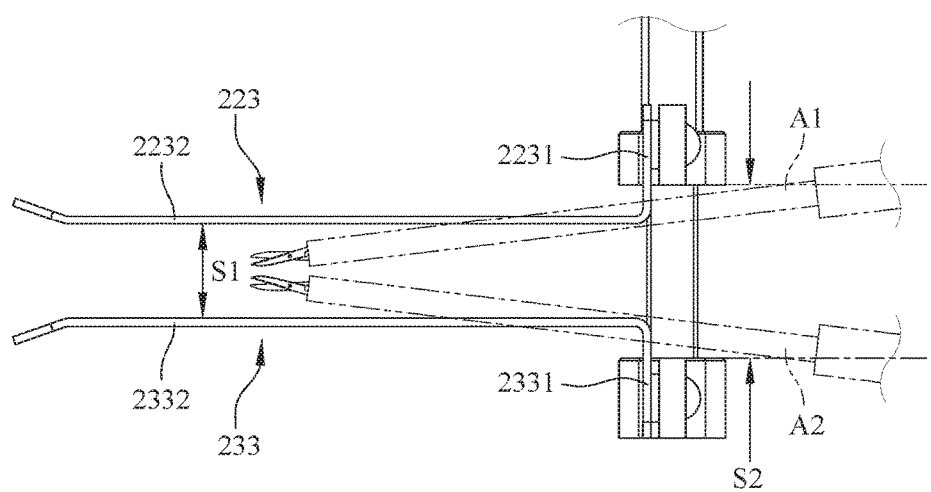
FIG. 5 is a schematic view of the wound opener according to an embodiment of the present invention, which shows the operating space.
Figure 6:
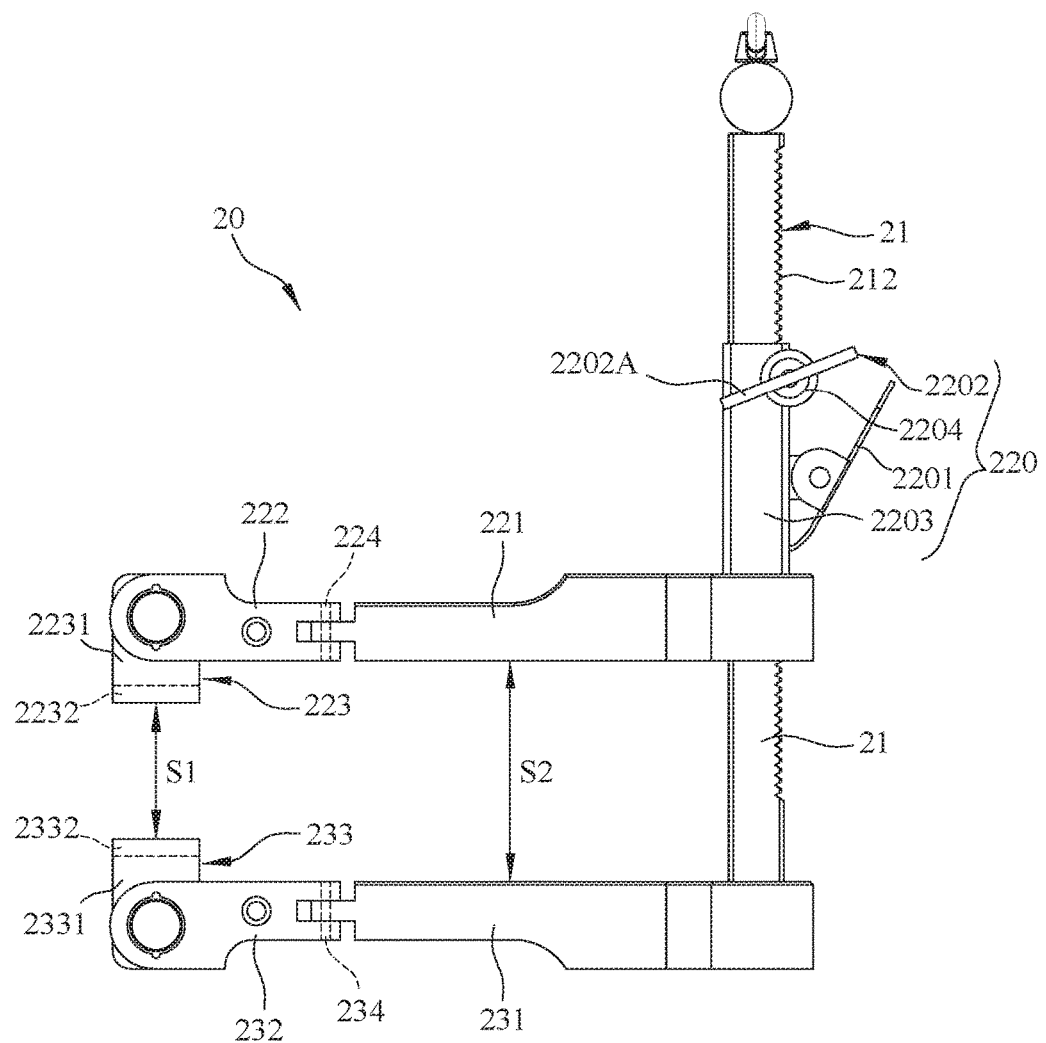
FIG. 6 is another side view of the wound opener according to an embodiment of the present invention, which shows the operating space.

FIG. 4 is a side view of the automatic mechanical wound opener, which is mounted on an operating bed 30, and FIG. 5 and FIG. 6 are schematic views of the wound opener according to one embodiment of the present invention, which show the operating space. Referring to FIGS. 4, 5 and 6, in actual use of the present invention, the first adjusting base 111 of the supporting unit 11 of the operating frame 10 is mounted at a side of the operating bed 30, and the wound opener 20 is fixed at an end of the operating frame 10 by the locking unit 211. The support rod 112 is adjusted to a proper position or height relative to the operating bed 30 before the operating frame 10 is mounted on the operating bed 30. In addition, an operational length of the extension rod 122 can be adjusted by the second adjusting base 121 according to the position of a patient.

After the supporting unit 11 and the connecting unit 12 of the operating frame 10 are adjusted to proper positions, the first drawing unit 22 and the second drawing unit 23 of the wound opener 20 are located near a wound of the patient for surgery and the plate parts 2232, 2332 of the first blade 223 and the second plate 233 are introduced into the wound for hooking head/neck soft tissues at both opposite sides. The first blade 223 connected to the adjusting unit 220 can be adjusted and moved along the fixed unit 21 by rotating the controlling member 2202 according to the wound size. The extension plate 2231 is used to adjust the position of the plate part 2232 of the first blade 223 at the upper side; and the extension plate 2331 is used to adjust the position of the plate part 2332 of the second blade 233 at the lower side. In addition, the slope of the plate part 2232 of the first blade 223 can be adjusted by pivoting the first blade 223 relative to the second arm 222, while the slope of the plate part 2332 of the second blade 233 can be adjusted by pivoting the second blade 233 relative to the second arm 232. Although the first blade 223 and the second blade 233 are adjusted to create a spacing S1 being approximately equal to the wound size, a larger and sufficient operating space S2 is created for ease of operation. Thus, endoscopes or robotic arms A1, A2 can be smoothly introduced to evaluate and treat lesions. The wound opener 20 helps operators (doctors) to do head and neck surgeries, therefore the wound size can be further reduced and the wound can be effectively concealed from visible.

Figure 8:
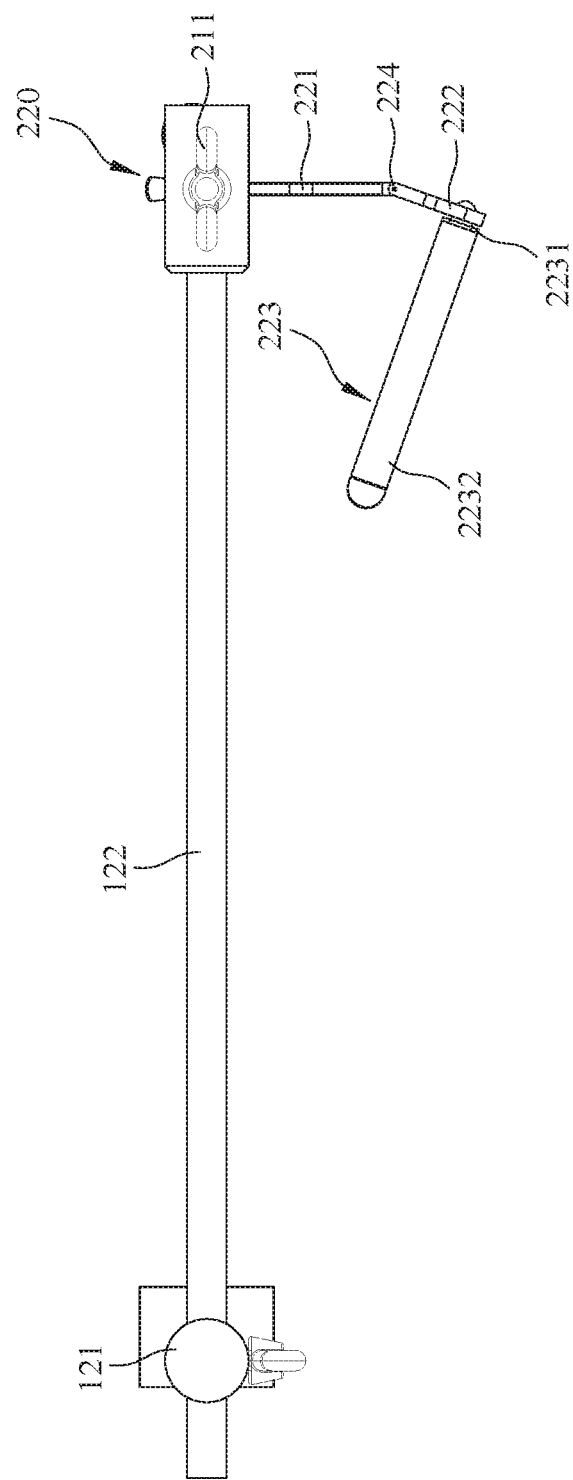
FIG. 8 is a top view of the automatic mechanical wound opener according to an embodiment of the present invention.
Figure 9:
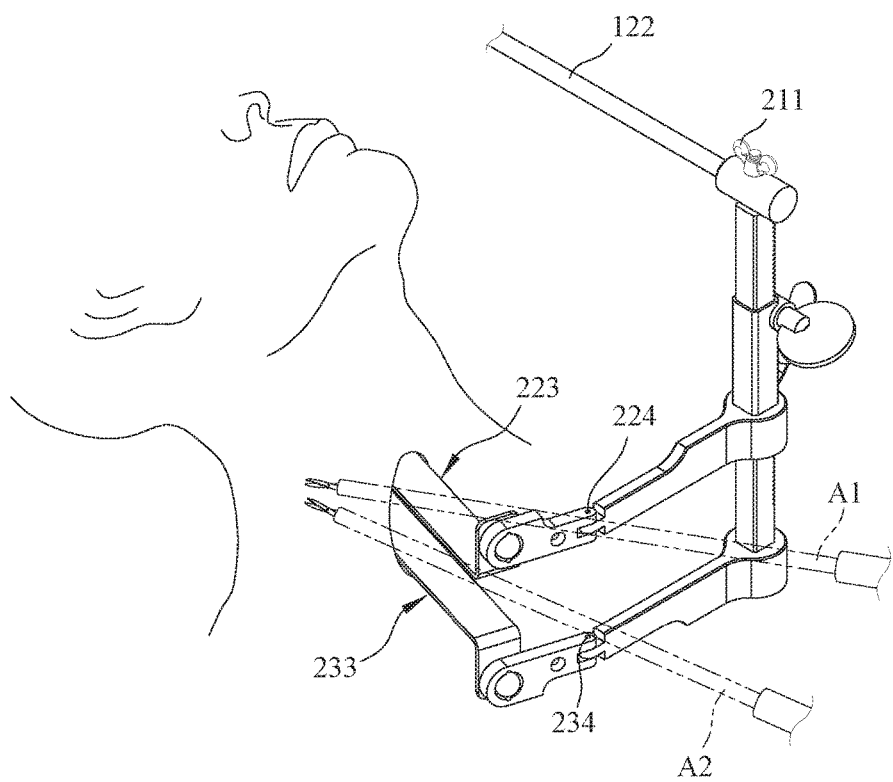
FIG. 9 is a schematic view showing the automatic mechanical wound opener according to an embodiment of the present invention during the surgery.

Referring to FIG. 8, which is a top view of the automatic mechanical wound opener according to one embodiment of the present invention. In this embodiment, the second arm 222 is adjusted around the pivot pin 224 to a desired angle to make the plate part 2232 of the first blade 223 move to a suitable position and create a more convenient and effective operative space. Therefore, the wound opener 20 according to the present invention can provide more flexible and convenient ways of operation and can be applied to surgery of various parts of body. As shown in FIG. 9, which is a schematic view showing the automatic mechanical wound opener according to an embodiment of the present invention during the surgery, for example, the robotic arms A1 and A2 can be easily operated in the created space.

To sum up, the present invention provides a device of automatic mechanical wound opener for head and neck surgery, where the mechanic wound opener can be used to reduce the size of a wound as small as possible, but still can provide a wider operative space for introducing endoscopes or robotic arms to evaluate and treat head and neck lesions. Accordingly, the objectives of facilitating surgical procedure, reducing the wound size, and effectively concealing the wound from visible can be achieved.

The preferred embodiments described herein are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A device of automatic mechanical wound opener for head and neck surgery, comprising:
    a wound opener comprising:
        a fixed unit; and
        a plurality of drawing units connected to the fixed unit, wherein the plurality of drawing units are movably connected on the fixed unit,
        wherein each of the drawing units includes a first arm, a second arm connected with the first arm, and a blade connected to the second arm; the first arm is connected to the fixed unit by one end thereof and to the second arm by the other end thereof; the second arm can be adjusted to a needed included angle relative to the first arm; and at least one of the blades comprises an extension plate connected to an end of a plane plate part of the blade, and the extension plate is connected to the second arm for shortening a spacing between the blade, to which the extension plate is connected, and the other blade paired thereto during operation, wherein the spacing is substantially smaller than an operating space formed between the first arm, the second arm of the drawing unit, comprising the extension plate, and the first atm, the second arm of the other drawing unit when paired thereto, and wherein the blade which the extension plate is connected to is substantially parallel to the other blade pairing thereto when operation;

wherein in each of the drawing units the blade is pivotally connected to the second arm;

wherein the drawing unit being movably connected on the fixed unit is moved along the fixed unit to and positioned at a desired position by an adjusting unit;

wherein the adjusting unit comprises a controlling member and a moving member, the moving member is sleeved on and surrounds the fixed unit and has a chamber for inserting the controlling member therein, and the controlling member comprises an operating handle and a plurality of teeth, and wherein the fixed unit has a plurality of dental grooves corresponding to the plurality of teeth of the controlling member; and wherein the controlling member is configured to be inserted from either side of the chamber, and the chamber includes opening on both sides that are configured to receive the controlling member.

2. The device according to claim 1, wherein the adjusting unit further comprises a clamp, the clamp is mounted on the moving member, and a tip of the clamp grips in the dental groove so that the adjusting unit is able to be fixed at a desired position.

3. The device according to claim 1, wherein in each of the drawing units the blade includes a knob disposed on the extension plate, and the second arm includes a hole for inserting the knob therein, thereby the blade can be pivoted relative to the second arm to adjust the slope of the blade.

4. The device according to claim 1, wherein the blade is shaped in the form of long plate.

5. The device according to claim 1, wherein in each of the drawing units the plane plate part of the blade is substantially perpendicular to the extension plate.

6. The device according to claim 1, wherein in each of the drawing units the first arm and the second arm are pivotally connected to each other.

7. The device according to claim 1, further comprising an operating frame, wherein the wound opener is fixed at an end of the operating frame.

8. The device according to claim 7, wherein the operating frame comprises a supporting unit and a connecting unit movably mounted on the supporting unit; and the wound opener is fixed at an end of the connecting unit.

9. The device according to claim 8, wherein the supporting unit comprises a first adjusting base and a support rod movably mounted on the first adjusting base.

10. The device according to claim 9, wherein the connecting unit comprises a second adjusting base and an extension rod; the second adjusting base is movably mounted on the support rod; and the extension rod is movably mounted on the second adjusting base.

11. The device according to claim 10, wherein the extension rod is substantially perpendicular to the support rod.

* * * * *